United States Patent [19]

Howard et al.

[11] 4,283,256

[45] Aug. 11, 1981

[54] METHOD AND APPARATUS FOR MEASURING THE STRENGTH OF THE AIR/FUEL MIXTURE SUPPLIED E.G. TO AN I.C. ENGINE

[75] Inventors: Peter Howard, Chelsea, Mich.; David Weetman, Seaford, England

[73] Assignee: Ricardo Consulting Engineers Limited, Shoreham-by-Sea, England

[21] Appl. No.: 128,314

[22] Filed: Mar. 7, 1980

[30] Foreign Application Priority Data

Mar. 15, 1979 [GB] United Kingdom ............... 09084/79

[51] Int. Cl.³ ............................................ G01N 27/58
[52] U.S. Cl. .................................. 204/1 T; 23/232 E; 60/276; 73/23; 123/489; 204/195 S; 422/98
[58] Field of Search ............... 204/195 S, 1 S, 195 R, 204/1 T; 123/489; 60/276; 73/23; 23/232 E; 422/98; 338/34

[56] References Cited

U.S. PATENT DOCUMENTS

| | | | |
|---|---|---|---|
| 3,791,936 | 2/1974 | Pebler et al. | 204/1 T |
| 3,958,937 | 5/1976 | Shibata et al. | 204/195 S X |
| 3,960,500 | 6/1976 | Ross et al. | 204/1 T X |
| 3,962,866 | 6/1976 | Neidhard et al. | 60/276 |
| 4,128,458 | 12/1978 | Obiaya | 204/1 T |

FOREIGN PATENT DOCUMENTS

1253676 11/1971 United Kingdom.
1470721 4/1977 United Kingdom.
1526887 10/1978 United Kingdom.

*Primary Examiner*—G. L. Kaplan
*Attorney, Agent, or Firm*—Cushman, Darby & Cushman

[57] ABSTRACT

An instrument for measuring the air/fuel mixture strength supplied to e.g. an I.C. engine comprises a primary catalytic reactor having a matrix of annular cross-section in whose bore is housed a secondary catalytic reactor and a zirconia oxygen sensor. Propane gas or other hydrocarbon fuel is mixed with air and the mixture passed through the primary reactor and catalytically combusted. A flow of the combustion products of the catalytic reaction is withdrawn and mixed with an equal flow of the engine exhaust gases, and the mixture is passed over the secondary reactor (heated by the primary catalytic reaction) to oxidize its oxidizable constituents, and the products of this secondary reaction are passed over the zirconia sensor (heated by the primary catalytic reaction) for measurement of the oxygen content. The output signal of the zirconia sensor is processed electronically and supplied to a digital indicator giving a direct reading of the equivalence ratio of the mixture supplied to the engine intake. The sample flows of exhaust gas and of reference gas are drawn at equal pressure differentials through similar coils of tubing in heat exchange relationship with the gaseous products of the primary catalytic reaction. The instrument can be used with a portable supply of propane gas for monitoring the air/fuel ratio of the mixture supplied to an automobile engine under road use conditions.

21 Claims, 4 Drawing Figures

METHOD AND APPARATUS FOR MEASURING THE STRENGTH OF THE AIR/FUEL MIXTURE SUPPLIED E.G. TO AN I.C. ENGINE

BACKGROUND OF THE INVENTION

This invention relates to apparatus and methods for measuring the strength of the air/fuel mixture supplied to a combustion system which operates on liquid or gaseous hydrocarbon fuel (referred to herein as a combustion system of the type specified).

The invention is particularly although not exclusively applicable to the measurement of the mixture strength of internal combustion engines, e.g. automobile engines. For some years now great pressure has been exerted on the automobile industries in several countries to reduce the amounts of noxious gas emitted from the exhausts of road vehicles, and the scope of legislation is widening progressively to cover all sizes and types of internal combustion engine.

A wide range of instruments has been developed for the measurement of the various components in engine exhaust gases such as carbon monoxide, nitrogen oxides, unburnt hydrocarbons, carbon dioxide and oxygen. These have been used for research and development testing to reduce the exhaust gas emissions, for the official testing of new vehicle models for compliance with the legal requirements, and for routine testing of random vehicles as they leave the production line.

Partly to minimise the quantity of NOx in the exhaust gases, and partly to attain improved fuel consumption, there is a growing tendency to operate gasoline engines with lean mixture strengths, i.e. with mixtures in which an excess of oxygen over that for stoichiometric combustion is present. Thus there is a growing demand for instruments for the ready determination of the mixture strength supplied to an engine. Such instruments must operate from the exhaust gases of the engine, and it is convenient to base the mixture strength determination on the direct measurement of the gas proportions present in the exhaust gases.

Existing methods mostly work satisfactorily for research, production and inspection tests within the factory. There is, however, a growing need for smaller, self contained, and portable instruments. These are needed to extend research and development tests for vehicles operating under a whole range of conditions on the road, including the effect of altitude, using various mixture control devices. At the same time, the need for strict enforcement of the emission laws continues during the service life of a vehicle, which creates a demand for relatively small, lightweight, self-contained, robust and portable instruments which are relatively easy to operate. Such instruments could facilitate garage maintenance, periodical car health tests, and police surveillance.

There is thus a need for a light, portable, self-contained instrument based on the analysis of the exhaust gas in an operating vehicle, and one which can be used to give a direct readout of the pertaining equivalence ratio or, with the addition of a suitable chart recorder, a continuous trace of equivalence ratio with time.

The term equivalence ratio is used to mean the ratio of the actual air/fuel ratio of the mixture supplied to the engine for combustion, to the stoichiometric air/fuel ratio for the fuel being used. Numeric values greater than unity for this ratio indicate weak mixture strength, i.e. that an excess of oxygen is present in the mixture. Values less than one indicates a deficiency of oxygen, i.e. a rich mixture.

SUMMARY OF THE INVENTION

According to the present invention from one aspect, an instrument for measuring the ratio of air to fuel supplied to a combustion system of the type specified, for combustion therein, comprises means for effecting the continuous complete combustion of a controlled supply of hydrocarbon heating fuel mixed with a oxygen-containing gas or gaseous mixture (referred to as air) to produce, as a reference gas, a continuous supply of gaseous combustion products containing a known proportion of free oxygen, means for mixing a sample flow of the exhaust gases from the combustion system with a flow of the reference gas in a controlled proportion, means for effecting the catalytic oxidation of the mixture of sample gas and reference gas, to oxidise any unburnt components derived from the sample flow in the mixture, whilst utilising the heat generated by the combustion of heating fuel and air to maintain the catalytic oxidation reaction, and a monitoring device for measuring the proportion of free oxygen in the gaseous reaction products of the catalytic oxidation reaction from which measurement together with predetermined data the said air/fuel ratio can be derived.

Very conveniently propane gas, which is readily available in compact bottled form, may be used as the hydrocarbon heating fuel for the instrument, enabling a compact and readily portable instrument which is independent of external energy sources to be provided. However other hydrocarbon fuels, liquid or gaseous, including alcohols may be used instead of propane gas.

An oxygen-sensing cell which comprises a solid-electrolyte oxide cell, for example a zirconia oxygen sensor, may be used to measure the oxygen content of the catalytic reaction products.

Many known oxygen-measuring instruments use the known characteristics of a zirconia solid electrolyte oxygen sensor cell to determine the concentration of oxygen present in a gas mixture. The element of this type of sensor is often essentially a thimble of zirconia whose characteristic of electrical conductivity with temperature has been varied by the addition of a stabiliser such as calcia, yttria, magnesia, etc. during manufacture. Thin layers of porous platinum are deposited on the inner and outer surfaces of the zirconia thimble to act as electrodes. It is found that a difference of electromotive force exists across this type of cell which is related logarithmically to the ratio of the oxygen partial pressure existing across the zirconia thimble. This effect is considerably enhanced if the zirconia thimble is heated to a high temperature. In this instrument when a zirconia oxygen sensor is used it will be operated at a temperature close to 700° C., and the heat generated by the combustion of the heating fuel and air may be used also to maintain the required elevated operating temperature of the zirconia sensor.

In practice it is convenient to use atmospheric air as a datum gas for the zirconia sensor cell since air has a virtually constant percentage of oxygen present, which is 21% or a concentration of 0.21. Accordingly a current of atmospheric air is passed through the inside of the zirconia thimble to act as a datum gas flow, whilst the outside of the thimble is exposed to a flow of the gas mixture to be monitored for oxygen concentration. The EMF across the zirconia cell, as the varying catalytic reaction gas mixture flows past the outside of the zirconia sensor, is used to monitor, or if required, to provide a continuous trace with time of, the free oxygen concentration in the catalytic reaction products.

The zirconia sensor output EMF bears a straight line relationship to the logarithm of the ratio of oxygen partial pressures on the two sides of the sensor as long as free oxygen is always present in the gases supplied to it.

In a preferred construction of the instrument of the present invention, the instrument includes a housing containing a primary catalytic reactor whose matrix is of annular cross-section having an open-ended central bore through which extends a central housing tube containing a smaller secondary catalytic reactor and the operative part of the monitoring cell, a controlled flow of the mixture of heating fuel and air being passed through the primary reactor outside the central tube, whereby the operating temperatures of the secondary reactor and of the monitoring cell are produced and maintained by the primary catalytic reactor which surrounds the secondary reactor and the operative part of the monitoring cell and heats the entire assembly, the mixture of sample and reference gas being passed through the central housing tube to transverse first the secondary reactor and then the monitoring cell.

Means are provided for withdrawing a sample flow of the reference gas leaving the primary reactor, and supplying a mixture of this sample and the sample flow of the exhaust gases from the combustion system, in known proportions, to the central housing tube, to traverse the secondary reactor and the monitoring cell.

For example, a gas flow circuit arrangement may be provided in which volumetric flows in known proportions of the sample gas and the reference gas, for example equal flows, are induced to flow under equal pressure differentials respectively through two similar coils of tube of known proportionate resistance to flow, for example equal resistances, the coils being in heat-exchange relationship with the combustion products of the catalytic reaction in the primary reactor, and the two flows after passing through the two coils are mixed and the mixture is passed through the central housing tube to traverse the secondary reactor and the monitoring cell.

Where the instrument is being used to measure the mixture strength of the intake of an I.C. engine, the output from the monitoring cell may be electronically processed to provide a direct indication on a meter or recording instrument of the equivalence ratio (as hereinbefore defined) of the combustible mixture being supplied to the engine or other combustion system.

The invention from another aspect comprises a method of measuring the ratio of air to fuel supplied to a combustion system of the type specified, for combustion therein, which method comprises effecting the continuous complete combustion of a controlled supply of a mixture of a hydrocarbon heating fuel and an oxygen-containing gas or gaseous mixture (referred to for convenience as air) to produce, as a reference gas, a continuous supply of gaseous combustion products containing a known proportion of free oxygen, mixing a sample flow of the exhaust gases from the combustion system with a flow of the said reference gas in a controlled proportion, effecting the catalytic oxidation of the said mixture of sample gas and reference gas, to oxidise any unburnt components derived from the sample flow in the mixture, whilst utilising the heat of combustion of the said mixture of heating fuel and air to maintain the catalytic oxidation reaction, measuring the proportion of free oxygen in the gaseous reaction products of the catalytic oxidation reaction, and using that measurement together with predetermined data to derive the air/fuel ratio of the combustible mixture being supplied to the combustion system.

BRIEF DESCRIPTION OF THE DRAWINGS

The invention may be carried into practice in various ways, but one specific embodiment thereof will now be described by way of example only and with reference to the accompanying drawings, in which.

DESCRIPTION OF THE PREFERRED EMBODIMENT

Figure 1:
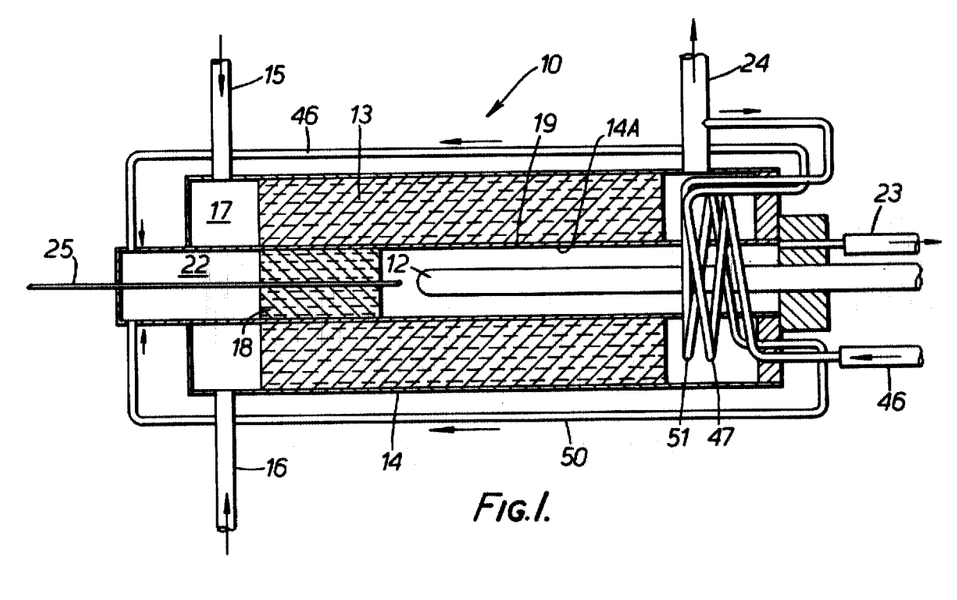
FIG. 1 is a diagrammatic sectional view of the catalytic oxidation and measuring sections of a portable instrument embodying the invention.
Figure 2:
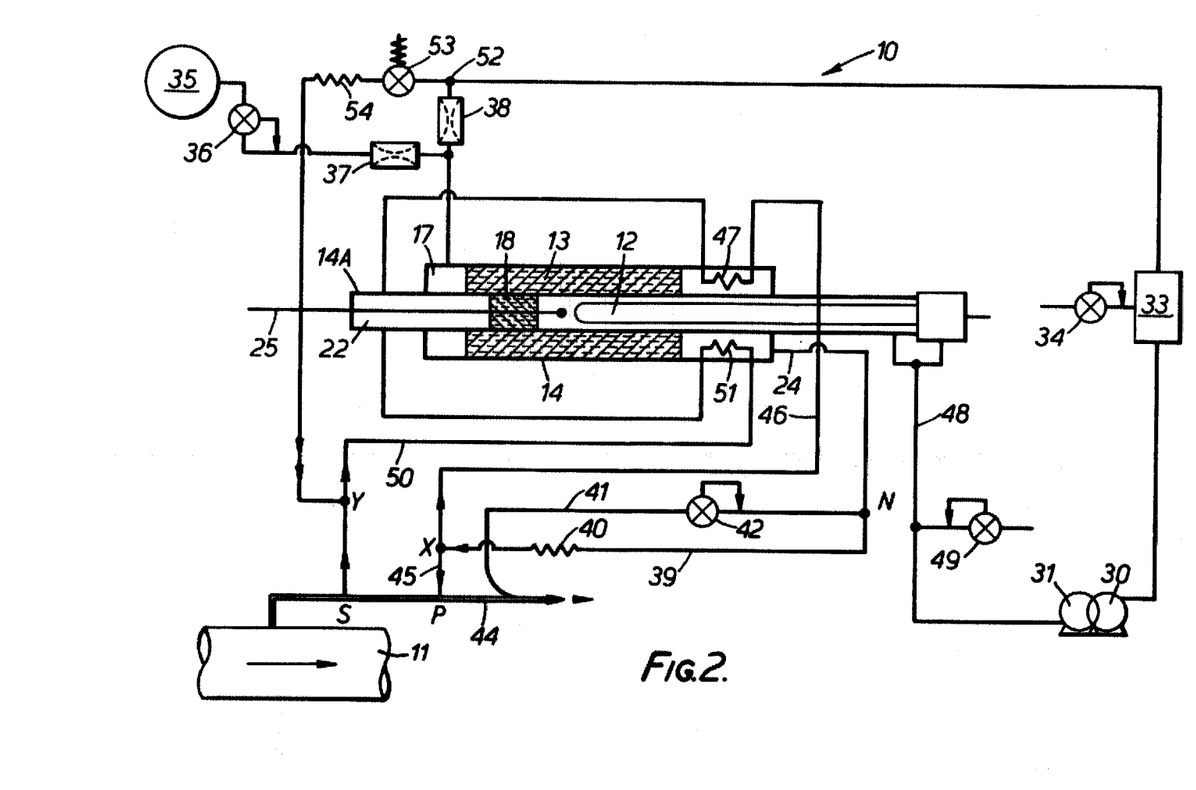
FIG. 2 is a schematic flow diagram showing the gas circuits and controls associated with the whole instrument of FIG. 1.

The portable instrument 10 shown in FIGS. 1 and 2 is for measuring directly the resultant oxygen content of a sample flow of exhaust gases from e.g. an I.C. engine after admixture with a known proportion of a separate reference gas containing only nitrogen, carbon dioxide and oxygen, and the passage of the resultant mixture through an oxidation catalyst matrix to oxidise such small quantities of unburnt carbon monoxide and/or hydrocarbons not burnt within the engine, and for deriving therefrom a direct measurement of the air/fuel ratio of the nominally gaseous charge supplied to the engine for combustion. The original exhaust gas sample is drawn from the I.C. engine exhaust duct 11 as shown in FIG. 2. The instrument comprises a quick-response solid oxide electrolyte analysis cell 12 of the zirconia sensor type, referred to as the zirconia sensor 12, whose operative portion is surrounded by a primary catalytic reactor 13 of annular section, in a housing 14. The housing 14 has an inlet 15 for air and an inlet 16 for heating fuel, in this case propane gas, the inlets 15 and 16 leading into a mixing chamber 17 in the outer annular part of the housing interior upstream of the primary reactor 13. A small secondary catalytic reactor 18 is housed in a central tube 14A of the housing which extends through the bore 19 of the annular primary reactor 13, the secondary reactor 18 lying upstream of the zirconia sensor 12 in the central tube 14A.

The two concentric catalytic reactors 13 and 18 are preferably of the monolithic matrix support type, on the surfaces of whose matrices is deposited a platinum or platinum-plus-additive type oxidation catalyst. The larger primary reactor 13 is used to oxidise the mixture of heating fuel and air supplied to the chamber 17 so as to heat the whole internal assembly and maintain the required operating temperature of around 700° C. required by the zirconia sensor 12. When starting from cold, a small electrical heater (not shown) is used locally to heat the matrix of the reactor 13, but once oxidation of the heating fuel-air mixture has started the process self-generates heat and the electrical heater can be turned off. This starting heater can be operated from a vehicle battery as required.

After "light-up" of the oxidation process of the heating fuel/air mixture, which is arranged to have an excess of oxygen present, and when the catalyst matrices have been heated up to the desired operating temperature, arrangements are made to take samples of equal volumes of gas at equal pressures from the heating fuel combustion products at 24 and from the engine exhaust system 11, respectively, and pass them separately through equal-resistance capillary tubing coils 51 and 47 into the space 22 in the central tube 14A to the left hand side of the small secondary oxidation catalyst matrix 18, where they mix together to pass over the bed of the catalyst 18. Here any oxidisable products remaining in the engine exhaust gas sample are oxidised to carbon dioxide or water. The fully oxidised combustion products pass by the outside of the zirconia sensor 12, which measures the oxygen concentration remaining in the gases, and leave the instrument at the exhaust 23. That proportion of the heating fuel combustion gases not mixed with the engine exhaust gas sample is exhausted to atmosphere at the primary bypass 24. A thermocouple 25 whose temperature-measuring tip is close to the zirconia sensor 12 is used first to ensure that temperatures close to 700° C. are maintained, using a direct-reading meter denoted as "Flame-Out Meter" 26 in FIG. 3. It is also used in conjunction with an analogue computer 62, also integral with the portable instrument 10, to correct the EMF output from the zirconia sensor 12 for minor excursions of temperature from the precalibrated operating value.

As described, the instrument uses a separate burnable fuel to preheat and then maintain the catalyst beds and zirconia sensor at the required operating temperature, and also to provide the reference gas to be mixed with the sample gas. Whilst the original thought was to use bottled propane or butane gas such as can be readily bought from retail outlets as the heating fuel, it would be possible, by making the appropriate detailed changes, to use other fuels, including liquid fuels, as the heating fuel, even for example the fuel on which the I.C. engine runs.

Figure 2A:
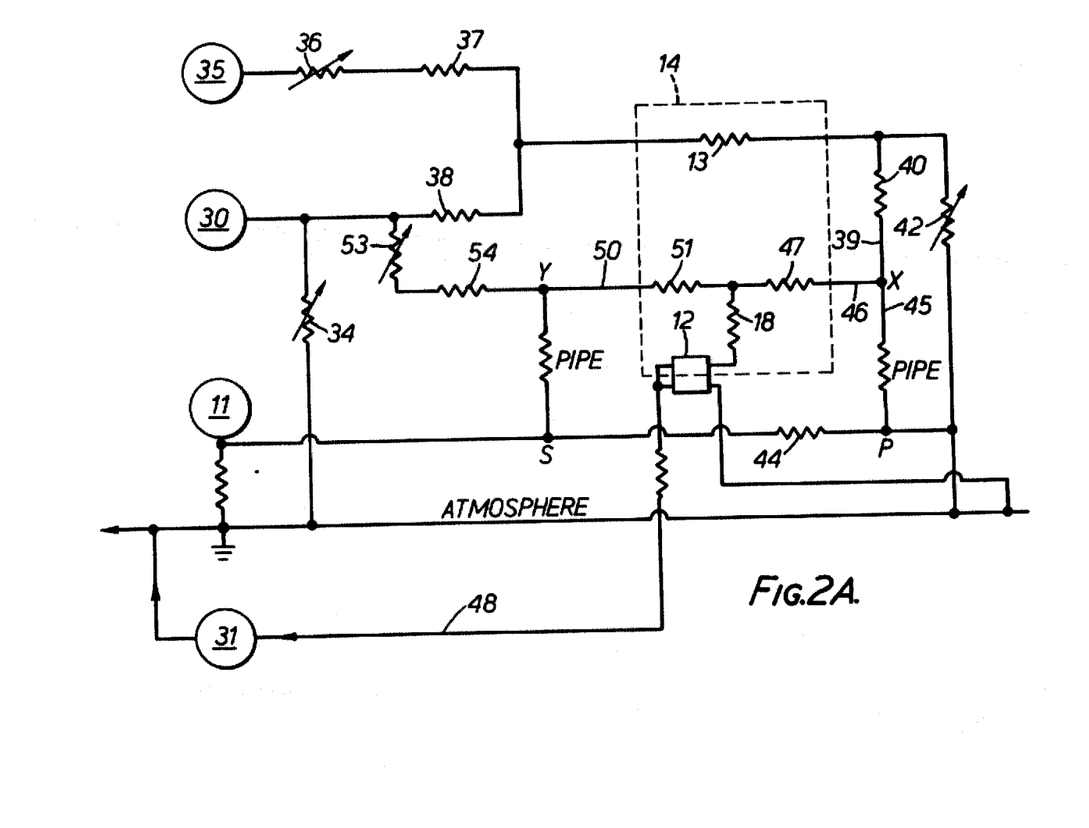
FIG. 2a is a diagram of an analogous resistive network corresponding to the gas flow circuit of FIG. 2.

The means for supplying the heating fuel, i.e. propane gas, and air together with the exhaust gas sample to the catalyst beds will now be described with reference to FIG. 2, which gives the schematic gas flow diagram for the complete instrument. FIG. 2A has been drawn as an analogous resistance network to assist understanding of FIG. 2.

In FIG. 2, an air compressor 30 and a vacuum pump 31 are driven from a common electric motor, not shown. Air delivered by the compressor 30 passes into a reservoir 33, the pressure in the reservoir being controlled by the adjustable automatic relief valve 34. The pressure is set to maintain a gauge pressure of between 1.1 and 1.5 bar, the actual pressure being dependent on the air/fuel ratio selected when setting up the instrument for testing and being also interrelated with the quantity of the heating fuel delivered from a supply bottle 35 via a control valve 36 and a critical flow orifice 37. The air supply from reservoir 33 also passes through a critical orifice 38. Downstream of their respective critical orifices the gas and air flows join, mix together, and pass into the chamber 17 upstream of the primary combustion (oxidation) catalyst matrix 13. (In FIG. 1 the gas and air flows are shown as separately entering the chamber 17 in the housing 14 and mixing in the chamber 17. Either arrangement may be used).

Downstream of the matrix 13 the products of the heating fuel combustion, which have been arranged to have oxygen still present, flow to the primary bypass 24 leading into the engine exhaust sampling pipe 44 at a point P downstream of the engine exhaust gas sampling point S, via a junction point N where two parallel flow routes exist. One path is via a pipe 39 having a flow restriction 40, and the other is via a pipe 41 with a pressure control valve 42. The flow through the pipe 39 ends in a Tee piece at a point X one branch of which connects with the exhaust gas sampling pipe 44 through a restrictive pipe 45 at a point P, whilst the second branch is connected to a pipe 46 which leads, via a coiled capillary pipe 47 immersed in the hot combustion products in the outer annular part of the housing 14 downstream of the primary reactor 13, to the chamber 22 at the upstream side of the secondary reactor 18. The pressure in the engine exhaust gas sampling pipe 44 at S and P will usually be slightly in excess of atmospheric pressure, and the pressure at the downstream side of the secondary reactor 18 is maintained at a slight negative pressure by means of a pipe 48 leading to the vacuum pump 31, with a control valve 49 in a Tee to maintain the pressure at a desired pressure below atmospheric. As a result, exhaust gases flow from point S through a pipe 50, via a second capillary 51 immersed in the hot combustion gases from the primary reactor to the chamber 22 on the upstream side of the secondary reactor 18. Since the pressures at points X and Y in the pipes 46 and 50 are arranged to be equal and the piping from these two points to have equal flow resistances, the volumes of primary reactor exhaust gases and of engine exhaust gases flowing in unit time through the capillary pipes 47 and 51 respectively will be equal. These flows mix in the chamber 22 and the mixture passes through the secondary reactor 18 where any combustible products from the engine exhaust are fully oxidised by the excess oxygen present in the oxygen-rich primary reactor combustion products.

Before running a test it is necessary to adjust the air-fuel ratio for the heating fuel combustion so that an adequate amount of oxygen is left in the primary reactor exhaust gases to oxidise any unburnt residuals present in the engine exhaust gases. For this purpose an auxiliary air supply, normally kept turned off, is tapped off at point 52 upstream of the critical orifice 38 to pass through an adjustable pressure valve 53 and through a capillary tube 54 to joint the normal exhaust sampling line 50 at point Y. Under calibration conditions the engine is stationary so only pure air can join the sampling line 50 at Y. Pressure adjustments are made, but as the pressures at X and Y are the same the volumes of pure air and primary reactor exhaust products meeting in chamber 22 are equal.

As has already been pointed out, an essential feature of the instrument is the use of a separate source of combustible vapour or gas mixed with an excess of air to heat the catalytic matrices to their operating temperature. The following description of the chemical background and computing arrangements is based on the use of a zirconia oxygen sensor 12, which is well known as an oxygen concentration sensor. It should be pointed out that sensors other than the zirconia one could be used to measure the oxygen concentration provided suitable modifications are made to the read-out circuitry.

Figure 3:
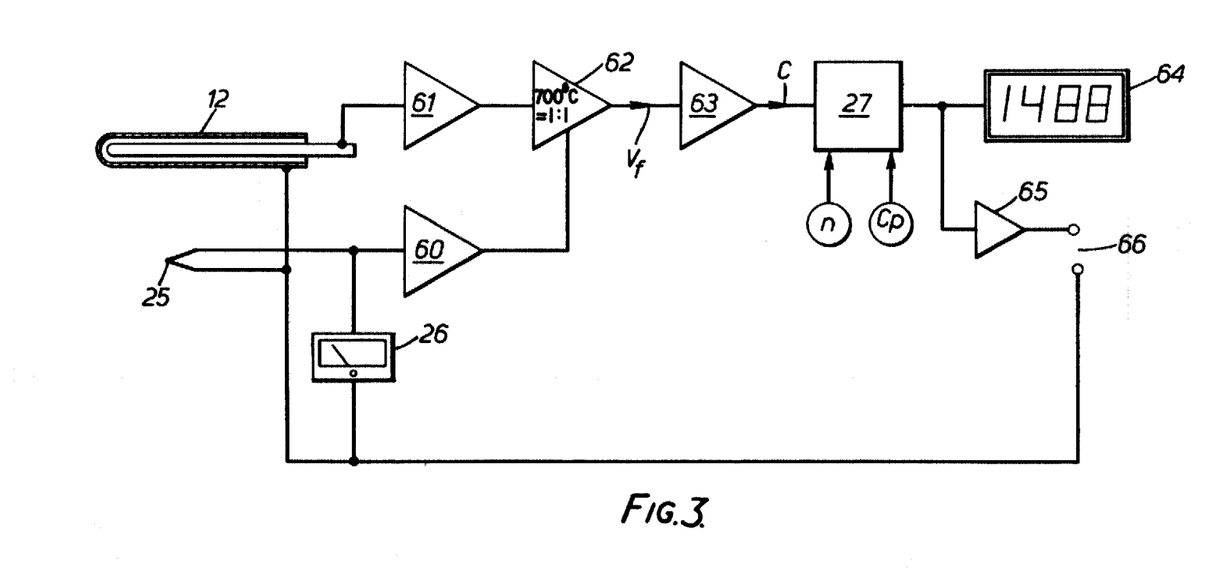
FIG. 3 is a schematic diagram of a signal conditioning circuit used in conjunction with the instrument of FIG. 2.

Signal Conditioning Circuit (FIG. 3)

When a zirconia sensor is operated with free oxygen present in a gas mixture supplied to it, an electromotive force (voltage) is generated across the cell wall, each side of which has a thin layer of porous platinum deposited on it to act as an electrode. The voltage generated follows Nernst's law:

$$V = K.T. \log_e (pO_2''/pO_2) \quad (1)$$

in which

V is the voltage generated
K = constant for a given cell
T = absolute operating temperature
$pO_2''$ = partial pressure of oxygen present in gas mixture being measured
$pO_2$ = partial pressure of oxygen present in datum gas. In this application this is atmospheric air.

It will be noted that for satisfactory operation the operating temperature for the zirconia cell 12 must be reasonably high. In the present case it is proposed that the operating temperature shall be around 700° C. (973° K.). However as the output from the zirconia sensor 12 is temperature-dependent the thermocouple 25 is used to monitor the actual working temperature.

Referring now to FIG. 3, the zirconia sensor 12 and thermocouple 25 are shown on the left hand side. The "flame out" meter 26 is a high-impedance millivoltmeter to allow a visual monitoring of the operating temperatures within the catalytic beds 13 and 18 immediately adjacent to the zirconia oxygen sensor 12.

The thermocouple 25 is connected to the high-impedance input of an amplifier 60 which contains circuits to linearise the signal from the thermocouple, since the thermocouple EMF is not quite linear with temperature. This is standard modern practice.

Now the output of the zirconia sensor 12 is only a small number of millivolts and is affected by the measuring circuit resistance. For this reason the sensor 12 is connected to the high-impedance input of a buffer amplifier 61.

The outputs from the amplifier 60 and the buffer amplifier 61 are connected to separate inputs of a temperature-compensating amplifier circuit 62 whose purpose is to increase or decrease the signal coming from the sensor cell 12 via the buffer 61 according to whether the thermocouple reading is below or above the desired reference temperature of 700° C. (973° K.). The output from amplifier 62 now gives a signal vf proportional to the logarithm of the ratio $pO_2''/pO_2$ at the standard temperature of 700° C. (973° K.)

Thus $$V_f = K_1 \log_e (pO_2''/pO_2) \quad (2)$$

where $K_1$ is the constant for the zirconia cell in use at a standard operating temperature of 700° C. combined with the electrical multiplying factors in the circuits used up to this stage. Equation (2) can be rearranged in the form:

$$(pO_2''/pO_2) = \text{Antilog}_e (V_f/K_1) \quad (2a)$$

The circuit 63 is a standard one to perform this antilogging process electrically.

Now $pO_2''/pO_2$ is proportional to the ratio of the volumetric proportion of oxygen in the measured sample to the proportion of oxygen present in the datum gas which is atmospheric air in this case. This is the value C for the antilogged output of the zirconia sensor 12.

Referring now to the computing and amplifying network 27, which may be of either analogue or digital type, two input values n and Cp are indicated. n is the known hydrogen/carbon ratio for the fuel being used by the I.C. engine under test, and Cp is the volumetric fraction of oxygen present as the result of the initial setting-up calibration prior to the use of the instrument for engine exhaust gas tests. Once set these values for n and Cp are constants during a particular test run.

The output signal from the computing network 27 can be used to provide a direct readout of the air-fuel ratio of the combustible mixture being supplied to the engine by means of a meter 64. The output from computer 27 may also be fed via an impedance matching buffer 65 to output sockets 66 to drive the 'pen' of a suitable recorder, thus providing a continuous trace with time of variations in air-fuel ratio.

Chemical Equations Involved in Obtaining Relationships for Readout

The engine fuel combustion equation is basically:

$$2CH_n + (2 + (n/2)) O_2 = 2CO_2 + n.H_2O$$

or volumetrically:

$$1CH_n + (1 + (n/4)) O_2 = 1CO_2 + (n/2).H_2O$$

But air contains v/v 21% $O_2$ and 79% $N_2$ i.e. 1 Part $O_2$ is associated with 3.76 parts $N_2$.

So 1 vol $CH_n$ + $\left(1 + \dfrac{n}{4}\right)$ $(O_2 + 3.76 N_2)$ vols air =

1 vol $CO_2$ + $\dfrac{n}{2}$ vols $H_2O$ + $3.76 \left(1 + \dfrac{n}{4}\right)$ vols $N_2$ Now if:

Heating fuel for instrument 10 has H/C ratio = $n_1$
Engine fuel has H/C ratio = n Engine Equivalence Ratio = $\dfrac{\text{(Actual air/fuel ratio)}}{\text{(stoichiometric air/fuel ratio)}} = \lambda$ Air/fuel ratio for heating fuel combustion = x
Then for the heating fuel combustion 1 vol $CH_{n1}$ + $x\left(1 + \dfrac{n_1}{4}\right)$ $(O_2 + 3.76n_2)$ vols =

1 vol $CO_2$ + $\dfrac{n_1}{2}$ vol $H_2O$ + $3.76\left(1 + \dfrac{n_1}{4}\right)$ vols $N_2$ +

$(x - 1)\left(1 + \dfrac{n_1}{4}\right)$ $(O_2 + 3.76 N_2)$ vols =

1 vol $CO_2$ + $\dfrac{n_1}{2}$ vol $H_2O$ +

$3.76\left(1 + \dfrac{n_1}{4}\right)$ $(x - 1 + 1)$ vols $N_2$ +

$(x - 1)\left(1 + \dfrac{n_1}{4}\right)$ vols $O_2$

For Engine:

$$1 \text{ vol } CH_n + \lambda \left(1 + \frac{n}{4}\right) (O_2 + 3.76 \, N_2) \text{ vols} \rightarrow$$

$$1 \text{ vol } CO_2 + \frac{n}{2} \text{ vols } H_2O + 3.76 \left(1 + \frac{n}{4}\right) \text{ vols } N_2 +$$

$$(\lambda - 1)\left(1 + \frac{n}{4}\right) \text{ vols } O_2 +$$

$$(\lambda - 1)\left(1 + \frac{n}{4}\right) 3.76 \text{ vols } N_2 =$$

$$1 \text{ vol } CO_2 + \frac{n}{2} \text{ vols } H_2O +$$

$$3.76 \cdot \lambda \left(1 + \frac{n}{4}\right) \text{ vols } N_2 +$$

$$(\lambda - 1)\left(1 + \frac{n}{4}\right) \text{ vols } O_2$$

Now combine equal volumes of heating fuel combustion products and those from engine exhaust.

Then unity volume of combustion products from the heating fuel + unity volume of exhaust (engine) products, deleting word 'vols' for convenience $$= \frac{CO_2 + \frac{n_1}{2} \cdot H_2O + 3.76\left(1 + \frac{n_1}{4}\right)(x) N_2 + (x-1)\left(1 + \frac{n_1}{4}\right) O_2}{1 + \frac{n_1}{2} + 3.76\left(1 + \frac{n_1}{4}\right)(x) + (x-1)\left(1 + \frac{n_1}{4}\right)} +$$

$$\frac{CO_2 + \frac{n}{2} H_2O + 3.76 \cdot \lambda \left(1 + \frac{n}{4}\right) N_2 + (\lambda - 1)\left(1 + \frac{n}{4}\right) O_2}{1 + \frac{n}{2} + 3.76\lambda\left(1 + \frac{n}{4}\right) + (\lambda - 1)\left(1 + \frac{n}{4}\right)}$$

and total volume = 2

Total volume of $O_2$ in 2 volumes of exhaust mixtures = (3)

$$\frac{(x-1)\left(1 + \frac{n_1}{4}\right)}{1 + \frac{n_1}{2} + 3.76\left(1 + \frac{n_1}{4}\right)(x) + (x-1)\left(1 + \frac{n_1}{4}\right)} +$$

$$\frac{(\lambda - 1)\left(1 + \frac{n}{4}\right)}{1 + \frac{n}{2} + 3.76\lambda\left(1 + \frac{n}{4}\right) + (\lambda - 1)\left(1 + \frac{n}{4}\right)} =$$

$$\frac{(x-1)}{\left[\frac{1 + \frac{n_1}{2}}{1 + \frac{n_1}{4}}\right] + 3.76x + (x-1)} +$$

$$\frac{\lambda - 1}{\left[\frac{1 + \frac{n}{2}}{1 + \frac{n}{4}}\right] + 3.76\lambda + (\lambda - 1)} =$$

$$\frac{(x-1)}{\left[\frac{\frac{1}{2}(2 + n_1)}{\frac{1}{4}(4 + n_1)}\right] + 4.76x - 1} +$$

$$\frac{(\lambda - 1)}{\left[\frac{\frac{1}{2}(2 + n)}{\frac{1}{4}(4 + n)}\right] + 4.76\lambda - 1} =$$

-continued $$\frac{(x-1)}{\left(\frac{n_1}{4 + n_1}\right) + 4.76x} + \frac{(\lambda - 1)}{\left(\frac{n}{4 + n}\right) + 4.76x}$$

So oxygen concentration per unit volume (as sensed by the zirconia cell 12 as a fraction) = C $$= \frac{1}{2}\left[\frac{(x-1)}{\frac{n_1}{4 + n_1} + 4.76x} + \frac{(\lambda - 1)}{\frac{n}{4 + n} + 4.76\lambda}\right] \quad (4)$$

But the first term in the bracket is the oxygen concentration due to the burning of the heating fuel used for heating which is determined during the initial set up of the air/fuel ratio meter for use with an internal combustion engine = $C_p$ say.

So Equation (4) may be written:

$$C = \frac{1}{2}\left[C_p + \frac{(\lambda - 1)}{\left(\frac{n}{4 + n}\right) + 4.76\lambda}\right] \quad (5)$$

From which $$2C - C_p = \frac{(\lambda - 1)}{\frac{n}{4 + n} + 4.76\lambda} \quad (6)$$

$$(2C - C_p)\left(\frac{n}{4 + n}\right) + (2C - C_p) 4.76 \lambda = \lambda - 1$$

$$(2C - C_p)\left(\frac{n}{4 + n}\right) + 1 = [1 - (2C - C_p)(4.76)] \lambda$$

So $\lambda = \dfrac{-\left(\dfrac{n}{4 + n}\right)(2C - C_p) + 1}{4.76(2C - C_p) - 1}$ Examining this formula:
  n is the hydrogen/carbon ratio of the engine fuel in use.
  Cp is anti-logged output from the zirconia sensor from the initial set-up with the heating fuel. This for a given engine test is a constant.
  C is the "live" working, virtually instantaneous, antilogged zirconia cell output after the mixing together of the heating fuel combustion products and the engine exhaust sample. This output represents the concentration of oxygen remaining in the combined products.

Setting $C_p$

Prior to starting the test engine the air supply and heating fuel are turned on and initially "ignited" by a brief period of electrical heating within the primary catalytic reactor matrix 13 (FIG. 1). Once the catalytic oxidation of the heating fuel-air mixture starts, the heating of the primary reactor becomes self-sustaining and the 'starting' electric heat is turned off. After a short warming up period to heat both catalytic matrices and the zirconia sensor up to about 700° C., the desired value for the concentration of oxygen in the combustion products of the heating fuel/air mixture can be set up by the adjustment of control valves 36 and 34. This set-up value is Cp which is then fixed for the subsequent engine test.

During the set-up period pure air is passed through the normal engine exhaust sampling pipe from junction Y is that the mixture passing through the second catalyst bed 18 consists of equal volumes of pure air and the combustion products of the heating fuel-air mix. The concentration of oxygen downstream of the reactor 18 is evaluated by the zirconia sensor 12.

The volumetric concentration of oxygen in pure air is 0.21 (21%). So with equal volumes of pure air and the products of heating fuel combustion the observed output reading from the zirconia sensor 12 will be:

$$C_{cal} = \tfrac{1}{2}(C_p + C_{air}) = \tfrac{1}{2}(C_p + 0.21)$$

where
$C_{cal}$ = the observed output from the zirconia sensor representing the oxygen concentration in the mixture
$C_p$ = oxygen concentration in the heating fuel combustion products
$C_{air}$ = oxygen concentration in pure air = 0.21
Thus $$C_p = 2 C_{cal} - 0.21.$$

which can be adjusted to give the desired value but, after the initial setting, remains constant for the duration of the subsequent engine test(s).

It will be understood that the instrument 10 may be compact and light in weight, perhaps of the order of 5 kg, and with a small cylinder of propane gas it forms an ideal unit for use in "in-vehicle" testing for research and development, e.g. for investigating carburation and fuel injection equipment particularly towards maximum leaness conditions.

The electrical power requirements of the instrument are small being only that needed for the initial ignition, solenoid valve operation and to drive the pumps required to move the sample and reference gases. The propane fuel may be obtained in commercially-available form, a small cylinder of 3 kg providing about 280 hours of operation. The instrument produces a reference gas of fixed $O_2$ content at constant temperature, by the controlled catalytic reaction of fuel and air, maintaining the required thermal equilibria for the catalytic reaction and for the zirconia sensor, allowing air to be used as the calibration gas and the zirconia sensor to give an absolute output from Nernst's equation. A very rapid response to transient changes (50 milliseconds) is obtained as a result of the direct sampling from the sample point to the analysis point, and a very wide range of air/fuel ratio can be covered by the simple adjustment of the proportion of excess oxygen in the reference gas. If the gas being investigated is very lean, e.g. the tail pipe gas of a gas turbine, the reference gas will be set just lean of stoichiometric to obtain reasonable sensitivity, since the tail pipe gas is likely to contain more oxygen than the reference gas, with the result that the mixture of sample and reference gas is just above the stoichiometric value.

With adjustment to the heating fuel and air metering devices, and the provision of means for atomising or vapourising liquid fuel, the insrument can be set to operate on a liquid fuel instead of propane, and can thus operate if necessary on the same fuel as that used by a process under investigation. This is particularly significant in its application to process control.

We claim:

1. An instrument for providing an indication of the ratio of air to fuel of a combustible mixture being supplied to a combustion system which operates on hydrocarbon fuel, for combustion therein, which instrument comprises:
    means for effecting the continuous complete combustion of a controlled supply of a hydrocarbon heating fuel with a controlled supply of an oxygen-containing gas to produce heat and a reference gas, said reference gas being a continuous supply of gaseous combustion products containing a known proportion of free oxygen,
    means for mixing a sample flow of exhaust gas from said combustion system with at least a sample flow of said reference gas in a controlled porportion, and
    means for effecting a catalytic oxidation reaction of the mixture of the sample flows of exhaust gas and reference gas to oxidise any unburnt components derived from the sample flow of said exhaust gas in the mixture,
    said means for effecting a catalytic oxidation reaction receiving said heat generated by the combustion of said heating fuel and said oxygen-containing gas to maintain said catalytic oxidation reaction.

2. An instrument as in claim 1 further comprising a monitoring device for measuring a proportion of free oxygen in the gaseous reaction products of said catalytic oxidation reaction from which measurement together with predetermined data the said air/fuel ratio is derived.

3. An instrument as claimed in claim 2, wherein said oxygen-containing gas is air, further comprising a portable supply of heating gas for supplying said heating fuel.

4. An instrument as claimed in claim 2 or 3, in which said monitoring device comprises a quick-response oxygen-sensing cell of the solid-oxide electrolyte type.

5. An instrument as claimed in claim 4, in which said monitoring cell compirses a zirconia oxygen sensor.

6. An instrument for measuring the ratio of air to fuel of a combustible mixture being supplied to a combustion system, comprising:
    a cylindrical housing,
    a primary catalytic reactor in secure contact alignment within part of said housing comprising a matrix of annular cross section, said matrix having an open-ended central bore, said cylindrical housing having an end thereof closed except for an aperture therein being substantially coaxial with and of substantially the same diameter as said bore, said primary catalytic reactor being disposed a predetermined distance therefrom for forming an annular first mixing chamber,
    a central housing tube extending through said bore and said aperture, a secondary catalytic reactor in secure contact alignment with part of said tube, said tube having an end thereof substantially closed, said secondary catalytic reactor being disposed a predetermined distance therefrom for forming a cylindrical second mixing chamber, a monitoring cell, said secondary catalytic reactor being disposed a predetermined distance from the other end of said tube, said monitoring cell being securely mounted in a space thereby provided, and said primary catalytic reactor thereby surrounding said secondary catalytic reactor and an operative part of said cell, whereby the operating temperatures of said cell and of said secondary catalytic reactor are produced and maintained by a catalytic reaction at said primary catalytic reactor, and a pair of substantially identical lengths of partly coiled heat exchange tubes, one of said tubes receiving a portion of a flow of combustion products from said primary catalytic reactor and the other of said tubes receiving a portion of a flow of exhaust gas of said combustion system, each of said tubes having a known proportionate resistance to gas flow, being in a heat exchange relationship with the combustion products of said primary catalytic reactor, and providing respective predetermined portions of the flow of said exhaust gas and the flow of said combustion products to said second mixing chamber, wherein a controlled flow of a heating fuel and air is supplied to said first mixing chamber for providing a mixture thereof to said primary catalytic reactor.

7. An instrument as claimed in claim 6, in which said pair of tubes are of equal flow resistance whereby the respective flows of gas through said tubes are of an equal volumetric flow rate.

8. A method of measuring the ratio of air to fuel of a combustible mixture being supplied to a combustion system operating on hydrocarbon fuel, for combustion therein, which method comprises the steps of:

effecting the continuous complete combustion of a controlled supply of a hydrocarbon heating fuel with a controlled supply of an oxygen-containing gas to produce heat and a reference gas, said reference gas being a continuous supply of gaseous combustion products containing free oxygen in a known proportion, mixing a sample flow of exhaust gas from said combustion system with a sample flow of said reference gas in a controlled proportion, effecting a catalytic oxidation reaction of said mixture of said exhaust gas and said reference gas, to oxidise any unburnt components derived from the sample flow of said exhaust gas in the mixture, said reference gas ensuring the presence of a proportion of free oxygen in the gaseous combustion products of said catalytic oxidation reaction over the range of air/fuel ratios of said combustible mixture, utilising the heat of combustion of said mixture of said heating fuel and said air to maintain said catalytic oxidation reaction, using a quick-response oxygen-sensing cell of the solid-oxide electrolyte type to measure the proportion of free oxygen in the gaseous reaction products of said catalytic oxidation reaction, and deriving an air/fuel ratio of the combustible mixture being supplied to the combustion system in accordance with predetermined data and the results of said measuring step.

9. A method as claimed in claim 8 in which the combustion of said heating fuel and said oxygen-containing gas is effected by means of a primary catalytic reactor.

10. A method as claimed in claim 9 in which the combustion of the mixture of said exhaust gas and said reference gas is effected by means of a secondary catalytic reactor, a matrix of said primary catalytic reactor surrounding said secondary catalytic reactor.

11. A method as claimed in claim 8, 9 or 10, in which said combustion system is an I.C. engine, and which includes the steps of:

automatically calculating from the said oxygen proportions of reference gas and reaction products and other data an equivalence ratio of said combustible mixture supplied to said engine, and providing a read-out of said equivalence ratio.

12. A method as claimed in claim 11 in which said measuring step further comprises the step of utilizing the heat of combustion of said heating fuel and said oxygen-containing gas to maintain said oxygen-sensing cell at an elevated operating temperature, the gaseous reaction products of said catalytic oxidation reaction being passed thereover.

13. An apparatus for providing an indication of an air/fuel ratio of a mixture supplied to a combustion engine for combustion therein, said instrument comprising:

a primary combustion chamber for receiving a heating fuel and an oxygen-containing gas in controlled proportions and effecting a continuous complete combustion of said fuel with said oxygen-containing gas to produce a reference gas having a known proportion of free oxygen and heat;

a secondary combustion chamber in thermal proximity with said primary chamber for receiving a controlled mixture of said reference gas and exhaust gas from said combustion engine and effecting a continuous complete combustion thereof by utilising the heat generated in said primary chamber to produce a gaseous reaction product, means for measuring the proportion of free oxygen in said gaseous reaction product and combining the information derived therefrom with known predetermined data for calculating said air/fuel ratio.

14. The apparatus of claim 13, wherein said primary combustion chamber comprises:

an inside surface of a substantially cylindrical housing;

an outside surface of an axially concentric central tube; and an annular primary catalytic reactor securely contained between said inside housing surface and said outside tube surface;

and wherein said secondary combustion chamber comprises:

an inside surface of said tube; and a substantially cylindrical secondary catalytic reactor securely contained within said inside tube surface and disposed within the opening through said primary catalytic reactor.

15. The instrument of claim 13 further comprising an oxygen sensor in thermal proximity with said primary chamber for receiving a flow of said gaseous reaction product from said secondary chamber and effecting a continuous measurement of the proportion of free oxygen thereof at a high temperature by utilizing the heat generated in said primary chamber, the sensitivity of said oxygen sensor being thereby significantly enhanced.

16. The apparatus of claim 15, wherein said primary combustion chamber comprises:
   an inside surface of a substantially cylindrical housing;
   an outside surface of an axially concentric central tube; and
   an annular primary catalytic reactor securely contained between said inside housing surface and said outside tube surface;
   wherein said secondary combustion chamber comprises:
   an inside surface of said tube; and
   a substantially cylindrical secondary catalytic reactor securely contained within said inside tube surface and disposed within the opening through said primary catalytic reactor;
   and wherein an operative portion of said oxygen sensor is securely supported within a space in said tube adjacent said secondary catalytic reactor and disposed within the opening through said primary catalytic reactor.

17. The apparatus of claim 14 or 16 further comprising:
   means for venting said reference gas from said primary combustion chamber;
   means for extracting from said reference gas venting means a predetermined flow of reference gas,
   means for extracting from an exhaust gas venting means a predetermined flow of exhaust gas, and
   means for mixing the predetermined flows of said reference gas and said exhaust gas to provide a controlled mixture thereof to said secondary combustion chamber.

18. The apparatus of claim 17, wherein:
   said reference gas extracting means and said exhaust gas extracting means respectively comprise substantially identical lengths of partly coiled heat exchange tubing through which respective proportional flows of reference gas and exhaust gas are induced to flow under substantially equal pressure differentials, said lengths of tubing having a known proportionate resistance to gas flow and being in heat exchange relationship with said reference gas at an output of said primary combustion chamber within said reference gas venting means, and
   said reference and exhaust gas mixing means comprises a chamber at one end of said tube adjacent said secondary catalytic reactor for receiving and mixing the proportionate flows of said reference gas and exhaust gs respectively.

19. The apparatus of claim 18, wherein said lengths of tubing are of equal flow resistance, whereby equal resistance volumetric flow rates are induced therein.

20. The apparatus of claim 14 or 16 further comprising means for mixing predetermined flows of said heating fuel and said oxygen-containing gas to provide a controlled mixture thereof to said primary combustion chamber.

21. The apparatus of claim 16, wherein said oxygen sensor comprises a solid oxide electrolyte having zirconia therein.

* * * * *